(12) United States Patent
Rohde

(10) Patent No.: US 6,294,329 B1
(45) Date of Patent: Sep. 25, 2001

(54) USE OF PRIMERS FOR UNIVERSAL FINGERPRINT ANALYSIS

(75) Inventor: Wolfgang Rohde, Busek (DE)

(73) Assignee: Max-Planck-Gesellschaft zur Forderung der Wissenschaften e.v., Berlin (DE)

( * ) Notice: Subject to any disclaimer, the term of this patent is extended or adjusted under 35 U.S.C. 154(b) by 0 days.

(21) Appl. No.: 09/117,525

(22) PCT Filed: Jan. 31, 1997

(86) PCT No.: PCT/EP97/00442

§ 371 Date: Nov. 2, 1998

§ 102(e) Date: Nov. 2, 1998

(87) PCT Pub. No.: WO97/28278

PCT Pub. Date: Aug. 7, 1997

(30) Foreign Application Priority Data

Feb. 2, 1996 (EP) .................................................. 96101515

(51) Int. Cl.$^7$ .............................. C12Q 1/68; C12P 19/34; C07H 21/04

(52) U.S. Cl. ........................... 435/6; 435/91.2; 536/24.3; 536/24.31; 536/24.32; 536/24.33

(58) Field of Search .................... 435/6, 91.2; 536/24.3, 536/24.33, 24.31, 24.32

(56) References Cited

U.S. PATENT DOCUMENTS 5,455,169 * 10/1995 Mullan ............................... 435/240.2

FOREIGN PATENT DOCUMENTS

| 10433748 | 6/1991 | (EP) . |
| 20443748 | 8/1991 | (EP) . |
| 10647718 | 4/1995 | (EP) . |
| 9308297 | 4/1993 | (WO) . |

OTHER PUBLICATIONS

Lehninger, A.L. et al. Principles of Biochemistry, 2nd edition. Worth Publishers, New York, NY, p. 329, 1993.*

I. Manninen et al., *Plant Molecular Biology*, vol. 22, pp. 829–846 (1993).

D. Lee et al., *Plant Molecular Biology*, vol. 15, pp. 707–722 (1990).

W. Rohde, "Improvement of coconut by biotechnology: application of molecular techniques to breeding and crop protection", *La Recherche Europëeenne au Service du Cocotier–Actes du Seminaire*, Montpellier, France, pp. 41–52 (Sep. 2–6, 1993).

A. Fukuchi et al., *Jpn. J. Genet.*, vol. 68, pp. 195–204 (1993).

M. D. Purgganan et al., *Molecular Ecology*, vol. 4 pp. 265–269 (1995).

W. Rohde, et al, "Genome Analysis of Cocos Nucifera L. by PCR Amplification of Spacer Sequences Separating a Subset of Copia–like EcoRI Repetitive Elements", J. Genet. & Breed. 49: pp. 179–186 (1995).

W. Rohde, et al, "An EcoRI Repetitive Sequence Family of the Coconut Palm Cocos Nucifera L. Shows Sequence Homology to Copia–like Elements", J. Genet. & Breed. 46: pp. 391–394 (1992).

(List continued on next page.)

Primary Examiner—Carla J. Myers
Assistant Examiner—Diana Johannsen
(74) Attorney, Agent, or Firm—Birch, Stewart, Koi & Birch, LLP

(57) ABSTRACT

The invention relates to the use of primers or primer pairs for DNA fingerprint analysis, wherein with the primers or primer pairs fingerprints are obtainable from humans as well as from animals as well as from plants as well as from microorganisms. The invention further relates to primers or primer pairs for the above-mentioned use.

36 Claims, 13 Drawing Sheets

OTHER PUBLICATIONS

Figures 1A, 1B:
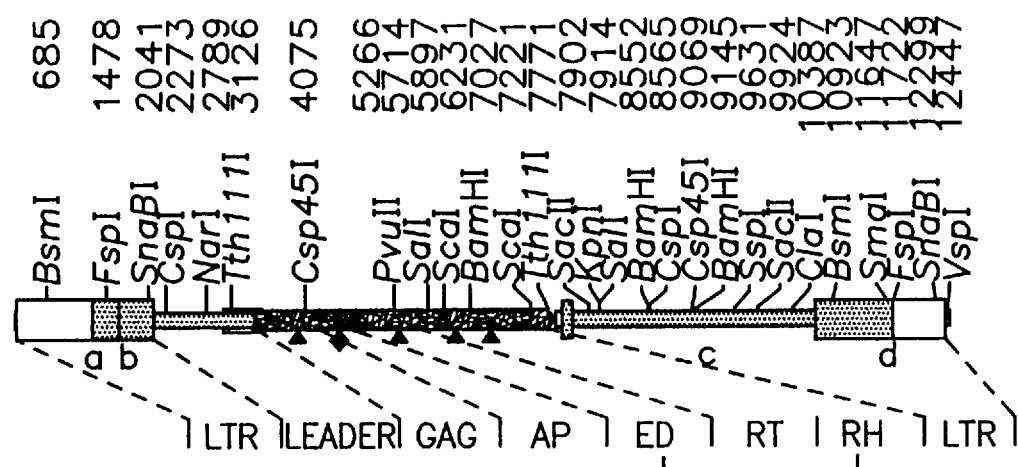

John Walsh, et al, "Fingerprinting Genomes Using PCR with Arbitrary Primers", Nucleic Acids Research, vol. 18. No. 24, pp. 7213–7218.

J. Sambrook, et al, "Molecular Cloning", A Laboratory Manuel Second Edition (Copyright 1989) pp. 11–11.57.

Rohde, W. Journal of Genetics and Breeding 50(3):249–261, Sep. 1996.*

Voytas, D.F. et al. Proc. Natl. Acad. Sci. USA 89:7124–7128, Aug. 1992.*

Newton, C.R. (ed.), PCR Essential Data, John Wiley & Sons, Chichester, p. 104–106, 1995.*

* cited by examiner

COPIA-LIKE COCONUT SEQUENCE

SEQUENCE LISTING

<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 1
aggaggtgaa taccttag                                                    18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 2
aaaatggcat agtctctc                                                    18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 3
gtcgacatgc catctttc                                                    18

```
<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 4
tatagtacct attgggtg                                                 18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 5
atatatggac ttaagcaagc                                               20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 6
gtattgtacg tggatgacat c                                             21

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 7
caacagtgct cccactga                                                 18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 8
tgctaggact ttcacaga                                                 18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 9
ttttctactt catgtctga                                                19
```

-continued

```
<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 10
aataaatcga tcatcgac                                                      18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 11
attcccatct gcaccaat                                                      18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 12
atgtcatcca cgtacaat                                                      18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:primer that
      hybridizes to copia-like sequences

<400> SEQUENCE: 13
cttctgtgaa agtcctag                                                      18
```

USE OF PRIMERS FOR UNIVERSAL FINGERPRINT ANALYSIS

This application is the national phase under 35 U.S.C. § 371 of prior PCT International Application No. PCT/EP97/00442, which has an International filing date of Jan. 31, 1997 and which designated the United States of America, the entire contents of which are hereby incorporated by reference.

The invention relates to the use of primers or primer pairs for DNA fingerprint analysis, wherein the use of the primers or primer pairs allows to obtain fingerprints from humans as well as from animals as well as from plants as well as from microorganisms. The invention further relates to primers or primer pairs for the above-mentioned use.

It is generally known that the presence of polymorphic and heterogenously dispersed repetitive sequences such as microsatellites is used for genetic analysis.

It is also well-known that retrotransposons such as copia elements of Drosophila and copia-like elements in other species of the animal and plant kingdom usually are present as multiple copies in the genomes. Repetitive genomic sequences of this type were used in the example of copia-like elements in pisum (pea) for the genetic analysis of this plant species (Lee et al., Plant Mol. Biol. 15 (1990), 707–722). This method designated OFLP is based on a copia-specific primer and a second primer of a sequence of the retrotransposon flanking pea genome for PCR amplification. This made it possible to amplify pea varieties by PCR amplification of specific elements of the pea copia family and to test for polymorphisms by separation of the non-radioactively labeled PCR products on an agarose gel and determine genetic relatedness. Also other retrotransposons, e.g. Tos1-1, Tos2-1 and Tos3-1 from rice have been used as molecular genetic markers for differentiation and identification of rice cultivars by RFLP-analysis (Fukuchi et al., Jap. J. Genetics 68 (1993), 195–204), while, however, also here it has been postulated that for other plant species their endogenous retrotransposons are isolated for use as a molecular marker. Another work (Purugganan and Wessler, Mol. Ecology 4 (1995), 265–269) uses a PCR-based method, which utilizes the variation of restriction sites for restriction enzymes in transposable elements for a fingerprint analysis. All these methods described in the prior art have, however, in common that the described genetic markers or primers cannot be universally used in humans, plants, animals or microorganisms. It is obvious that the provision of such genetic markers or primers would offer essential advantages in many areas of modern biology or medicine.

Thus, the problem underlying the present invention was to overcome the above-mentioned drawbacks of the prior art and to provide methods and means which allow for a maximum degree of universal applicability of a minimum amount of primers or genetic markers for a fingerprint analysis of species from the plant and animal kingdom as well as of humans.

The solution to this problem is provided by the embodiments characterized in the claims.

It has surprisingly been found that the primers which hybridize with copia-like elements in coconut (*Cocos nucifera* L.) and which in this system permit a fingerprint analysis can also be successfully used in many other species of the animal and plant kingdom as well as in humans and even in microorganisms including yeast. This finding permits to universally use said primers for fingerprint analysis in the whole animal and plant kingdom as well as in humans and in microorganisms.

Figure 2:
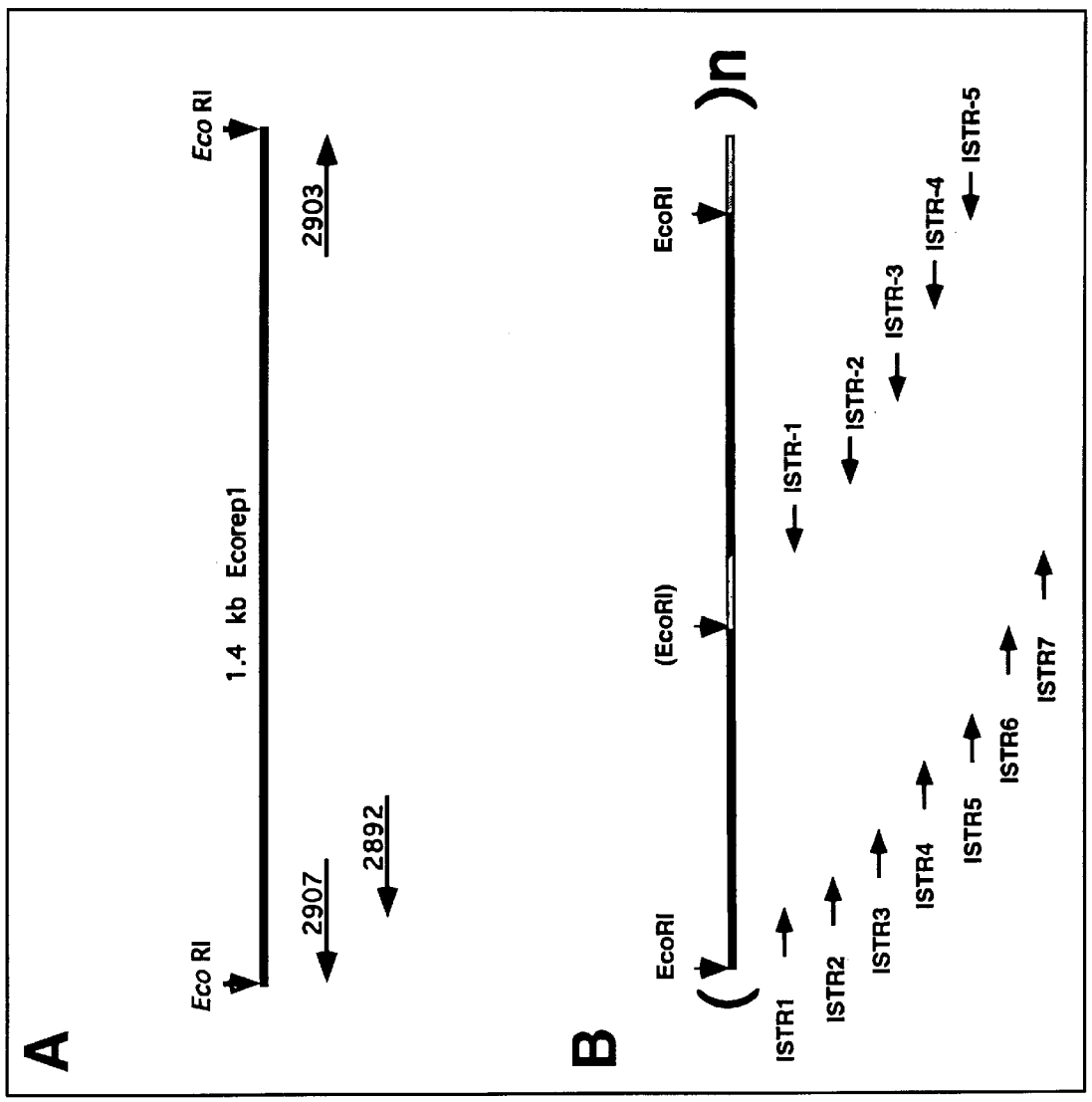
Figure 2A:
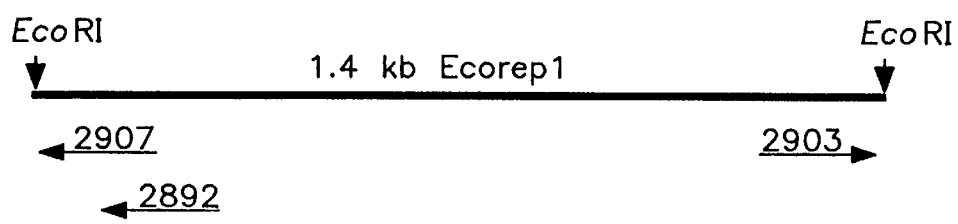
Figure 2B:
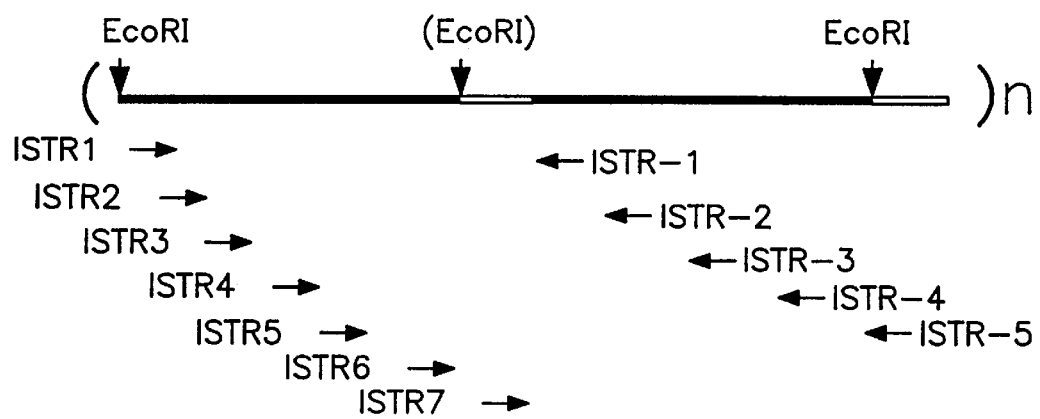

Thus, the present invention relates to the use of a primer or primer pair for DNA fingerprint analysis, characterized in that the primer or primer pair permits a fingerprint from humans as well as from animals and plants as well as from microorganisms, wherein the primer or primer pair hybridizes with a DNA which is comprised in the copia-like element of coconut (*Cocos nucifera* L.) as represented in FIG. 2B.

In this connection, the surprising results of the present invention are achieved with arbitrary combinations of different primers of opposite polarity with the only requirement that they hybridize with the copia-like element represented in FIG. 2B, as well as with the use of a single primer which, due to the repetition of the copia-like elements, albeit in $5'\rightarrow3'/3'\rightarrow5'$ orientation of two adjacent elements and not, as represented in FIG. 2B, in $5'\rightarrow3'/5'\rightarrow3'$ orientation, likewise provides the highly polymorphic fingerprints. It is self-evident that the aforementioned definition for the primers includes that they also hybridize to DNAs from other organisms as long as they contain DNA sequences which correspond to DNA sequences from the above-mentioned copia-like element.

The requirements for hybridization of the primer and subsequent amplification is derivable to the person skilled in the art without inventive effort from the prior art and the following examples.

The primers of the invention are preferably 15 to 25 nucleotides in length. The invention, however, can also be carried out with primers which are shorter or longer.

The present finding is even more surprising since as a rule the prior art started from the assumption that primers can only be used for reliable fingerprints in taxonomically narrow limits.

In the prior art Rohde et al. (J. Genet. & Breed. 46 (1992), 391–394) it is described that highly repetitive sequences having homology to copia elements described in other species exist in the genome of coconut (*Cocos nucifera* L.), which sequences are visible as two DNA bands, 1.3 and 1.4 kilobases in length, respectively, after restriction of isolated genomic DNA with the restriction enzyme EcoRI and separation on an agarose gel. Three of these "Ecorep"-designated DNA fragments were sequenced after subcloning and sequence deviations could be determined. Attempts to use these differences for the genetic analysis of different coconut types by use of Ecorep sequences as a molecular probe in RFLP analysis or by sequence specific PCR primers were not successful (Rohde et al., J. Genet. & Breed. 46 (1992), 391–394; Rohde in: "La Recherche Europeene au Service du Cocotier—Actes du Seminaire—8–10 septembre 1993, Montpellier". CIRAD (Collection: Colloques du CIRAD), Montpellier, pages 41–52).

Recently it was found for three coconut types that subfamilies of these 1.3 and 1.4 kilobase Ecorep sequences exist, in which these elements are clustered in the coconut genome, i.e. they represent tandem repeats, and in which usually at least one of the two expected EcoRI restriction sites at the ends of the sequence previously defined as "spacer region" is absent (Rohde et al., J. Genet. & Breed. 49 (1995), 179–186) from the previously identified elements (Rohde et al., J. Genet. & Breed. 46 (1992), 391–394). This spacer region shows high homology to the copia-like BARE-1-element from barley (FIG. 1A; Manninen and Schulman, Plant. Mol. Biol. 22 (1993), 829–846). Thus, the subfamily of copia-like sequences in the coconut genome represent tandem repeats, which display homology to the endonuclease and reverse transcriptase RNAse H region of a copia or copia-like element (see FIG. 1B). The observed sequence deviations in the elements of the subfamily could now—in contrast to the above-described attempts for the Ecorep sequences—be used for a genetic analysis in coconut by appropriate PCR primers. This method for a genome analysis in coconut was designated as ISTR (inverse sequence tagged repeat) analysis.

It was now surprisingly found that this subfamily with its highly conserved sequence appears to be ubiquitous in the plant and animal kingdom since the use of identical ISTR-primers (see also Table 1), which were developed on the basis of coconut sequences determined by us, obtained high polymorphic DNA fingerprints for other plant species as well as for animals and humans as well as for microorganisms. In this context, not only a multitude of polymorphic markers can be discovered which segregate in the progeny ("single locus/multiple allele"-markers) but also new polymorphic markers arise (individual specific markers), which, for example, are present neither in the father nor in the mother in control cross-breedings (for example cattle, sheep) and which can be possibly ascribed to recombination events or to the amplification of specific genomic regions. Conclusively, each fingerprint is unique for the individual progeny from identical parents. In the field of human biology it could be demonstrated that this also holds true for identical twins for which several of the used ISTR primer pairs display fingerprints that are different from each other (see FIG. 8).

Thus, a preferred embodiment of the use according to the invention is characterized in that with the primer or primer pair a fingerprint is obtainable with DNAs from the entire animal and plant kingdom, comprising (a) the animal kingdom with all its subkingdoms, preferably Metazoan including the subphylum of the vertebrates, preferably the class of Mammals, including in particular the family of the Hominids and the family of the Bovidae, including the species *Bovis tourus* and *Ovis aries* as well as all races and varieties which are derivable from the corresponding species;

(b) the plant kingdom with all its subkingdoms, preferably Mycobionta and Cormobionta, among the latter preferably the division of the Spermatophyta, therein preferably the class of Monocotyledonae with its families of the Arecaceae and its representatives of the species *Cocos nucifera* or the family of Poaceae with its representatives of the species *Hordeum vulgare* and *Zea mays*, in addition most preferably the class of the Dicotyledonae with its families, for example Solanaceae and its representatives of the species *Solanum tuberosum, Nicotiana tabacum, Petunia hybrida*, or e.g., the family of Brassicaceae with its representatives of the species *Brassica napus* or the family of the Chenopodiaceae with its representative *Beta vulgaris* or the family of the Vitaceae with its representative *Vitis vinifera* as well as all varieties and cultivars which are derivable from the corresponding species; and (c) humans; and (d) microorganisms comprising prokaryotic microorganisms, preferably gram-positive bacteria such as, e.g., lactic acid bacteria, sarcina and coryneform bacteria and gram-negative bacteria such as, e.g., Neisseria and enterobacteria, and eukaryotic microorganisms comprising fungi, preferably Phycomycetes such as, e.g., Phytophthora and Ascomycetes such as, e.g., yeasts.

A particular advantage of the use according to the present invention is that fingerprints of comparable resolution and sensitivity can be visualized with DIG labeled PCR products directly in the gel without the generally used transfer of the DNA fragments onto membranes (Southern blot) well-known in the art. Thus, the present invention allows to prepare such fingerprints in a simple way (separation of the PCR fragments in a sequence gel, direct detection in the gel, computer-aided data analysis by directly scanning the sequence gel) without the use of radioactivity.

Thus, a further preferred embodiment of the use according to the invention is characterized in that the DNAs to be analyzed is amplified with the primer or primer pair via PCR and subsequently separated on a gel according to the length of the PCR products.

From the prior art the person skilled in the art knows how to choose the conditions for an appropriate PCR. Also a method for the separation of PCR amplified DNAs on an electrophoresis gel which preferably is a polyacrylamide gel is known from the prior art.

In a particularly preferred embodiment, the gel is a sequencing gel. The preparation of sequencing gels is also well-known in the art and, for example, described in Sambrook et al., "Molecular Cloning, A Laboratory Handbook". CSH Press, Cold Spring Harbor, 1989.

In a further preferred embodiment, the use according to the invention is characterized in that in a further step a Southern blot is performed and the DNAs transferred onto the membrane are visualized by hybridization with a probe.

This embodiment is an alternative to the above-described embodiments. It requires more time and/or money and the handling of radioactivity, however, it is perfectly suitable for laboratories which have a less elaborate lab equipment, for example have no scanner with a connected computer. The performance of Southern blots as well as hybridizations with an appropriate probe are also well-known in the art and are, for example, described in Sambrook et al., loc. cit.

In a further particularly preferred embodiment of the use according to the invention, the probe is the primer or the primer pair of the invention.

Since the primers are part of the amplified DNA, the detection of the bands on the membrane used for Southern Blot can be easily performed.

In a further preferred embodiment of the use according to the invention, the primer or primer pair is labeled.

In a particularly preferred embodiment of the invention, the label is a non-radioactive label, in particular digoxigenin, biotin and fluorescence dye, a dye or a radioactive label, in particular $^{32}$P.

In particular, the labeling of the primers with digoxigenin and the dyeing of the DNA directly in the gel after amplification and gel electrophoretic separation of the DNA can be performed by all laboratories or interested breeders on the basis of a low budget equipment (PCR reaction, electrophoresis on sequence gels) and without the use of radioactivity. Storage and processing of the data is preferably performed by direct reading of the dyed and dried gel by a scanner into a computer. Furthermore, the possibility exists to develop specific primers to obtain allele specific amplification products by re-isolation of the PCR products of the sequencing gel and their re-amplification and sequencing.

In a further preferred embodiment of the invention, the primer displays the sequence as depicted in Table 1.

These primers are preferred examples of primers which were used by the inventors in previous fingerprint analyses. It should, however, be pointed out that also other primers can be used which hybridize to the sequence schematically represented in FIG. 2B and which is described in more detail in Rohde et al., 1992 loc. cit., and Rohde et al., 1995 loc. cit. Moreover, according to the invention, it surprisingly turned out that all previously tested primers which hybridize to this region can produce a reliable fingerprint in plants as well as in animals as well as in humans as well as in microorganisms.

In a further preferred embodiment, the use according to the invention is characterized in that the fingerprint analysis is used for studying biodiversity, genetic relatedness, taxonomy, and, in particular, in the field of forensic medicine, breeding, protection of plant varieties, gene library management, population genetics and for studies on the evolution.

Finally, the invention relates to primers for the use according to the invention, characterized in that the primers display any one of the sequences represented in Table 1.

The Figures show:

FIG. 1: Region of a copia-like element Bare-1 present in the genome of barley (FIG. 1A, from Manninen and Schulman, Plant. Mol. Biol. 22 (1993), 829–846) which was found as a tandem repeat copia-like sequence (Rohde et al., J. Genet. & Breed. 49 (1995), 179–186) in the genome of coconut (Cocos nucifera L.) (FIG. 1B).

(A) Diagram of the copia-like BARE-1 element from barley. ED: Endonuclease; RT: Reverse transcriptase; RH: RNAse H.

(B) Location of repetitive copia-like sequences from coconut relative to homologous sequences of the barley BARE-1 element. The hatched region characterizes the position of the recently found "spacer region" (Rohde et al., J. Genet. & Breed. 49 (1995) 179–186).

FIG. 2: Amplification of the "spacer region" between adjacent copia-like sequences in the coconut genome (A) and approximate position of previously used primers for the ISTR analysis (B).

(A) For the amplification for cloning and sequencing of the regions between two adjacent copia-like elements in the coconut the primer pairs ISTR5/ISTR-1 (SEQ ID NOS: 5 and 9) and ISTR5/ISTR-2 (SEQ ID NOS: 5 and 10) were used. The direction of arrow heads designates the 5'→3' orientation of the oligodeoxynucleotides used.

(B) Usually, each primer is between 18 and 20 nucleotides in length and was synthesized in analogy to the sequence of the Ecorep1 element (Rohde et al., J. Genet. & Breed. 49 (1995) 179–186). The primers provided with "-" are complementary to the coding sequence of the copia element and can be combined with any primer of the "plus" series for the ISTR analysis.

Figure 3:
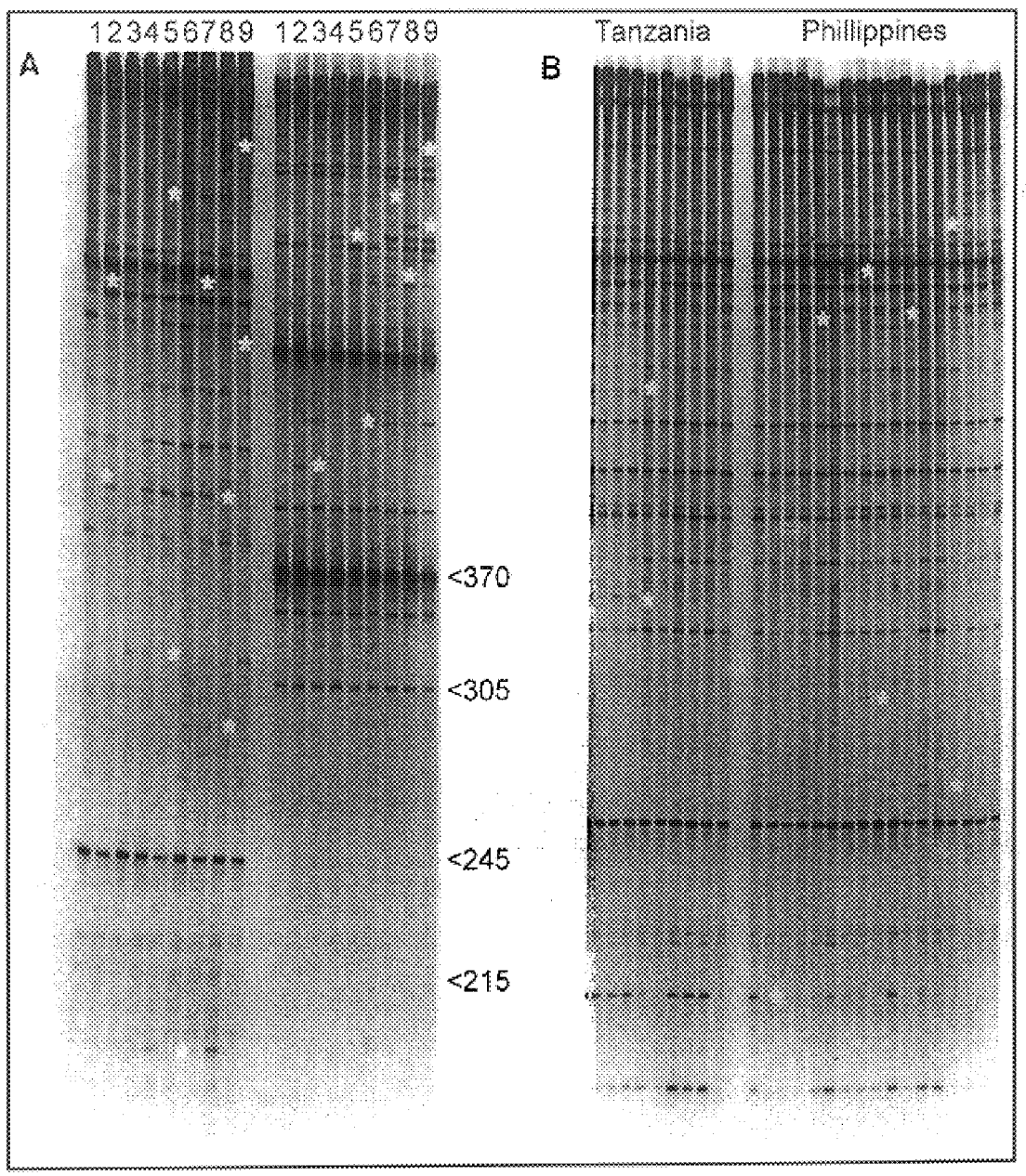

FIG. 3: ISTR analysis of populations exemplified by coconut (from Rohde et al., J. Genet. & Breed. 49 (1995) 179–186).

(A) In lanes 1 to 7, single palm trees of an East African Tall (EAT) population were characterized by ISTR analysis with primer pairs ISTR5/ISTR-2 (SEQ ID NOS: 5 and 10) (left) and ISTR5/ISTR-1 (SEQ ID NOS: 5 and 9) (right), respectively. Lanes 8 and 9 are control analyses of a single Rennell Island Tall (RLT)- or Pemba Red Dwarf (PRD)-palm tree.

(B) ISTR analysis of two Malayan Yellow Dwarf (MYD)-populations from Tanzania and the Philippines with the primer pair ISTR5/lSTR-2(SEQ ID NOS: 5 and 10).

Figure 4:
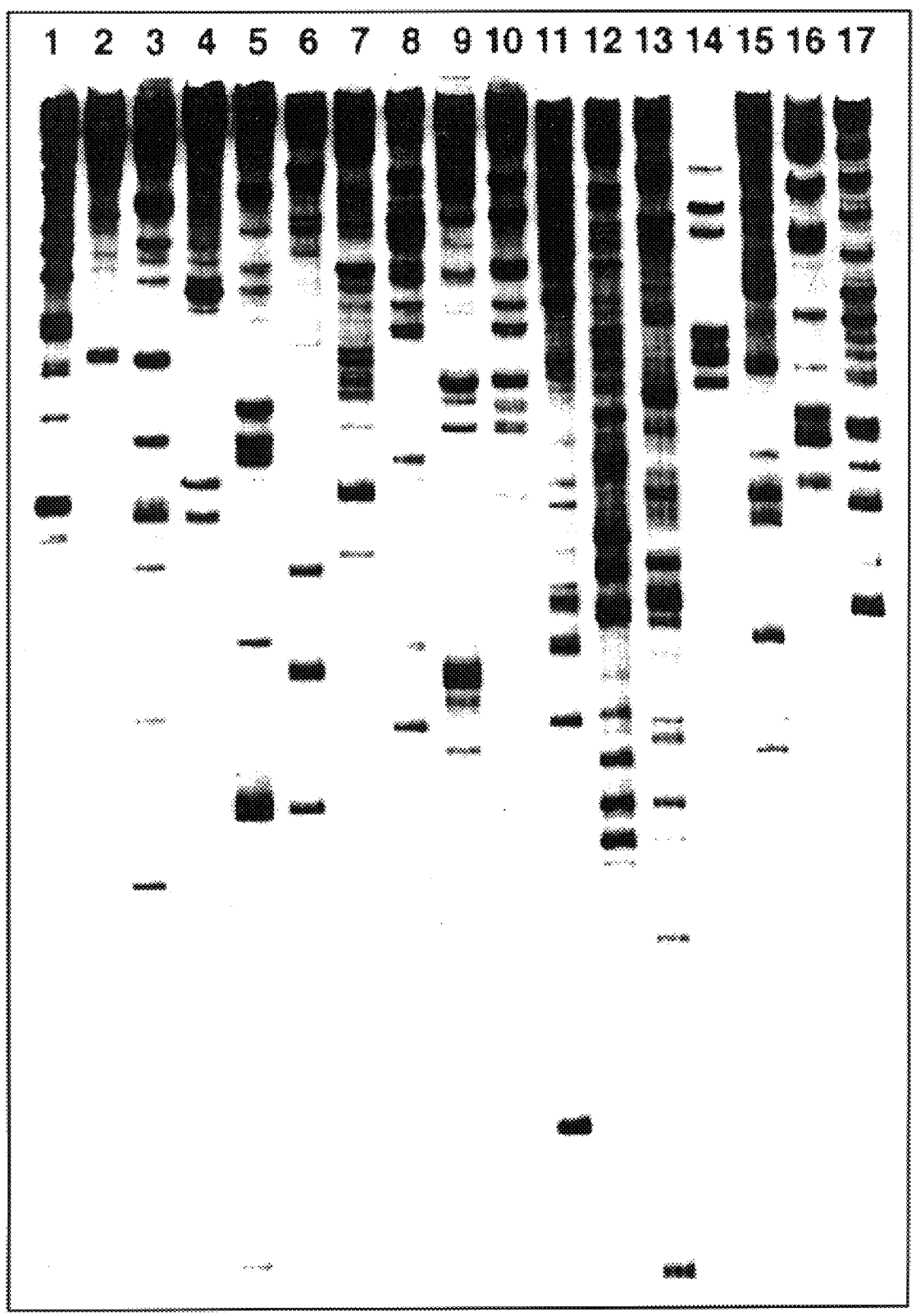

FIG. 4: General application of ISTR primers in the plant kingdom.

DNA of different plant species was subjected to amplification with primers ISTR5/ISTR-2(SEQ ID NOS: 5 and 10). The ISTR products in the separate lanes correspond to the following plants:

1: tobacco, 2: barley, 3: potato, 4: maize, 5: snap dragon, 6: Arabidopsis, 7: rape seed, 8: Craterostigma, 9: petunia, 10: parsley, 11: sisal, 12: Milala palm, 13: Borassus palm, 14: coconut palm, 15: sugar beet, 16: Cuphea, 17: yeast.

Figure 5:
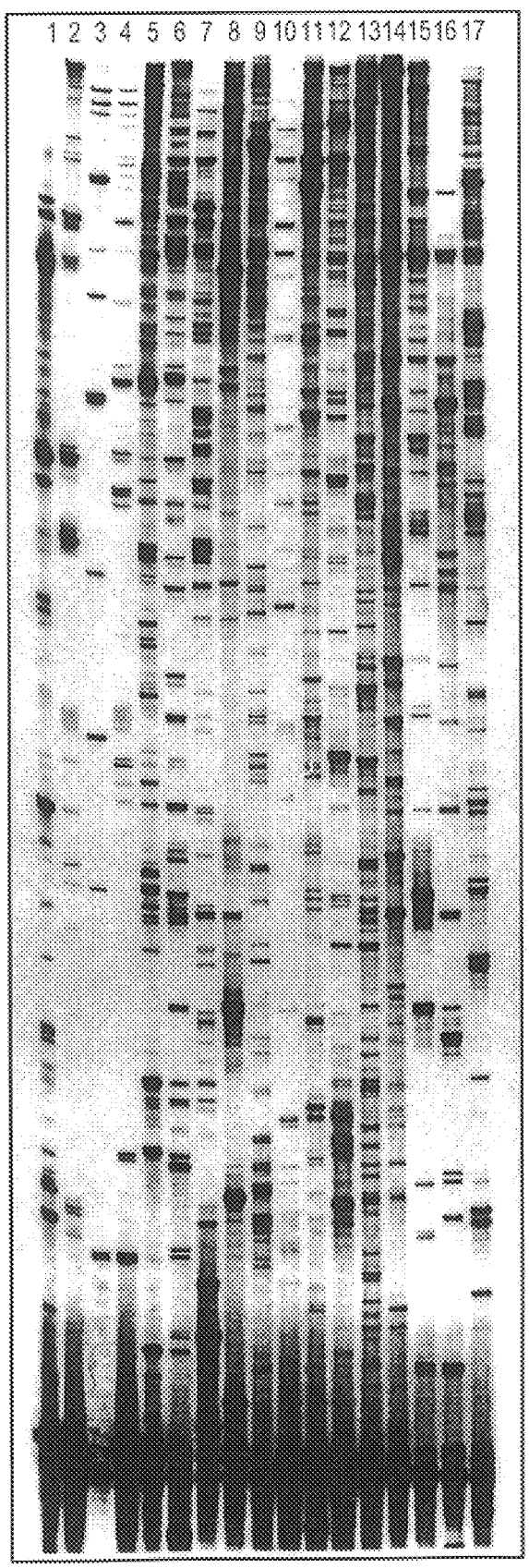

FIG. 5: ISTR analysis of individual members of the Arecaceae (Palmae). DNAs of 17 different palm trees were subjected to a standard PCR reaction with primers. ISTR5/ISTR-2 (SEQ ID NOS: 5 and 10) and separated on a 4% PAGE gel. The PCR products in each lane correspond to the following plants:

1: Hyphaene petersiana Mart., 2: Bismarckia nobilis Hildebrandt & H. Wendl., 3: Eugeissona utilis Becc., 4: Korthalsia echinometra Becc., 5: Mauritiella aculeata (H. B. & K.) Burret, 6: Nypa fruticans Wurmb., 7: Pseudophoenix sargentii H. Wendl. ex Sarg., 8: Oraniopsis appendiculata (F.M. Bailey) J. Dransf., Irvine and N. W. Uhl, 9: Socratea exorhizza (Mart.) H. Wendl., 10: Halmoorea tripatha J. Dransf. & N. W. Uhl., 11: Cyrtostachys peekeliana Becc., 12: Deckenia nobilis H. Wendl., 13: Oncosperma tigillarium (Jack) Ridley, 14: Syagrus amara (Jacq.f.) Mart., 15: Attalea allenii H. E. Moore ex L. H. Bailey, 16: Scheelea insignis (Mart.) Karsten, 17: Asterogyne martiana (H. Wendl.) H. Wendl. ex Hemsley.

Figure 6:
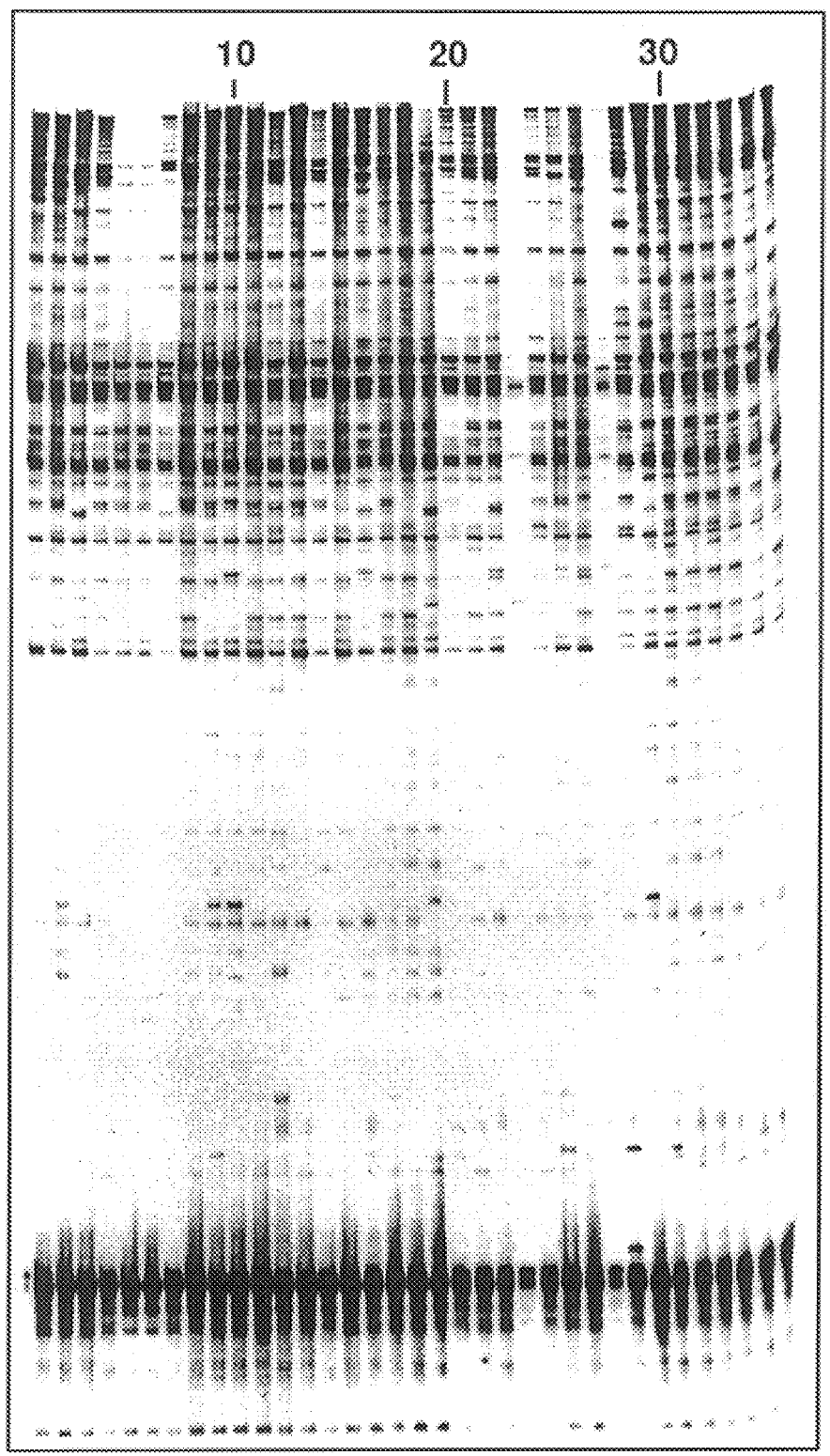

FIG. 6: ISTR analysis of barley varieties.

DNAs of 35 different barley genotypes were amplified in a standard PCR reaction with primers ISTR5/ISTR-2 (SEQ ID NOS: 5 and 10) and the PCR product was separated on a 4% PAGE gel. In the individual lanes the PCR products of the following plants were applied:

1: Fiction, 2: Kaskade, 3: Red, 4: Georgie, 5: Alexis, 6: Marinka, 7: Flash, 8: Portikos, 9: Aura, 10: Gimpel, 11: Prisma, 12: Gitane, 13: Gavotte, 14: Manila, 15: Pilastro, 16: Masto, 17: Torrent, 17: Torrent, 18: Thibault, 19: Onice, 20: Mette, 21: Robur, 22: Probidor, 23: Tania, 24: Mario Otter, 25: Nico, 26: Magie, 27: Vogelsanger Gold, 28: Tekto 2002, 29: Asse, 30: Calcaroides-C15 (ex Bonus), 31: calcaroides-b2 (ex Bonus), 32: calcaroides-b19 (ex Bonus), 33: Bonus, 34: Christina, 35: Nudinka.

Figure 7:
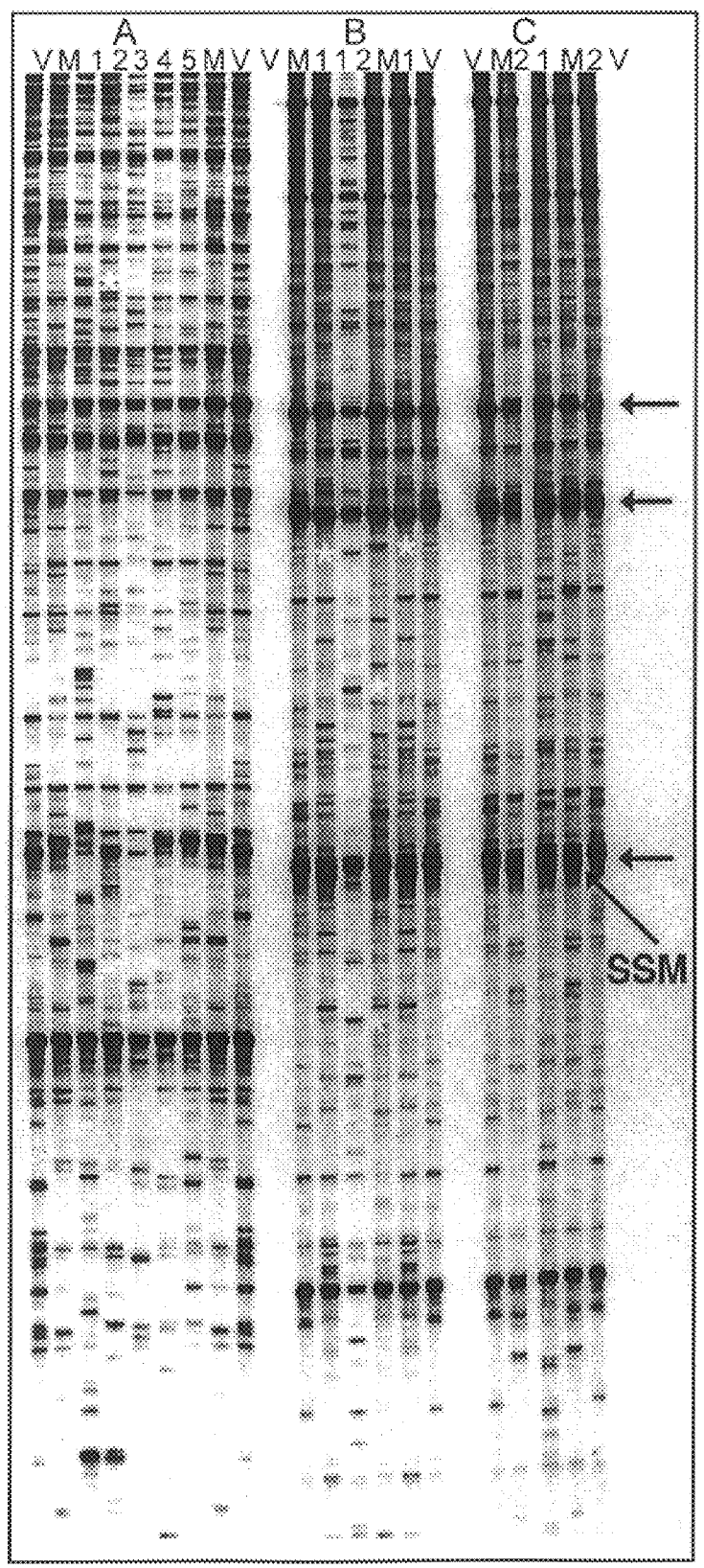

FIG. 7: Analysis of a cattle family (A) and two sheep families (B, C).

(A) Five offspring as well as both mother and father of 3 cattle family were subjected to ISTR analysis with the primer pair ISTR5/ISTR-2(SEQ ID NOS: 5 and 10). V: Father, M: Mother. The individual offspring are numbered. The arrow points out a marker which is not present in all individuals of the offspring.

(B, C) Analysis of two sheep families with offspring of a cross-breed between the identical father and mother M1 (B) as well as mother M2

(C). Arrows indicate segregating ISTR markers; asterisks point to individual-specific markers, which are present neither in the parents nor in the brothers and sisters.

GSM: Marker (lower band of the triplet), which cosegrates with the male sex. V: Father. The individual offspring of the different breedings are numbered.

Figure 8:
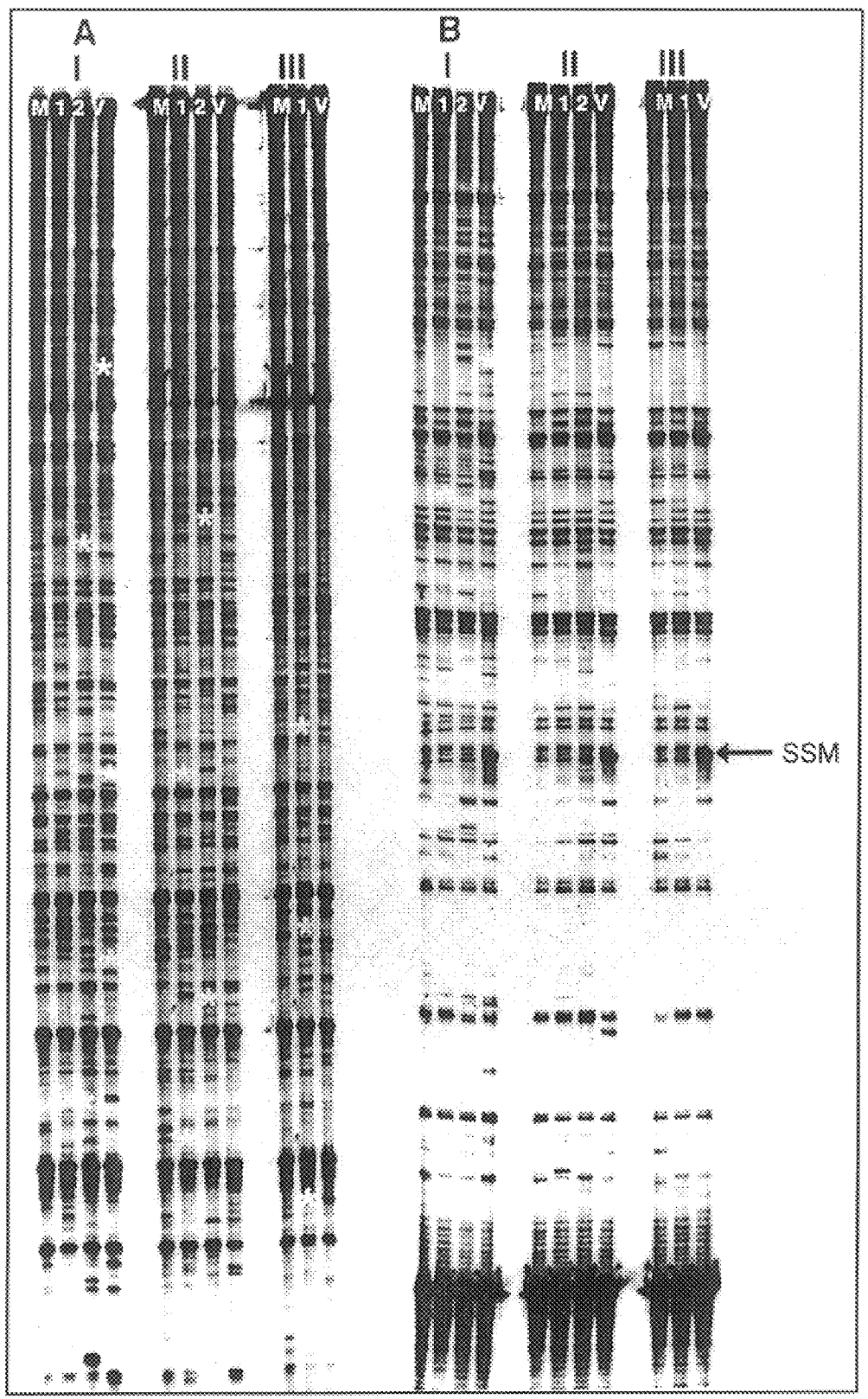

FIG. 8: Analysis of three human families I, II and III with different primer pairs.

(A) ISTR analysis with the primer pair ISTR6/ISTR-1 (SEQ ID NOS: 6 and 9).

(B) ISTR analysis with the primer pair ISTR6/ISTR-2 (SEQ ID NOS: 6 and 9).

V: Father of offspring; M: Mother; SSM: sex-specific marker. The offspring are numbered. The two offspring of families I and 11 are identical twins.

Figure 9:
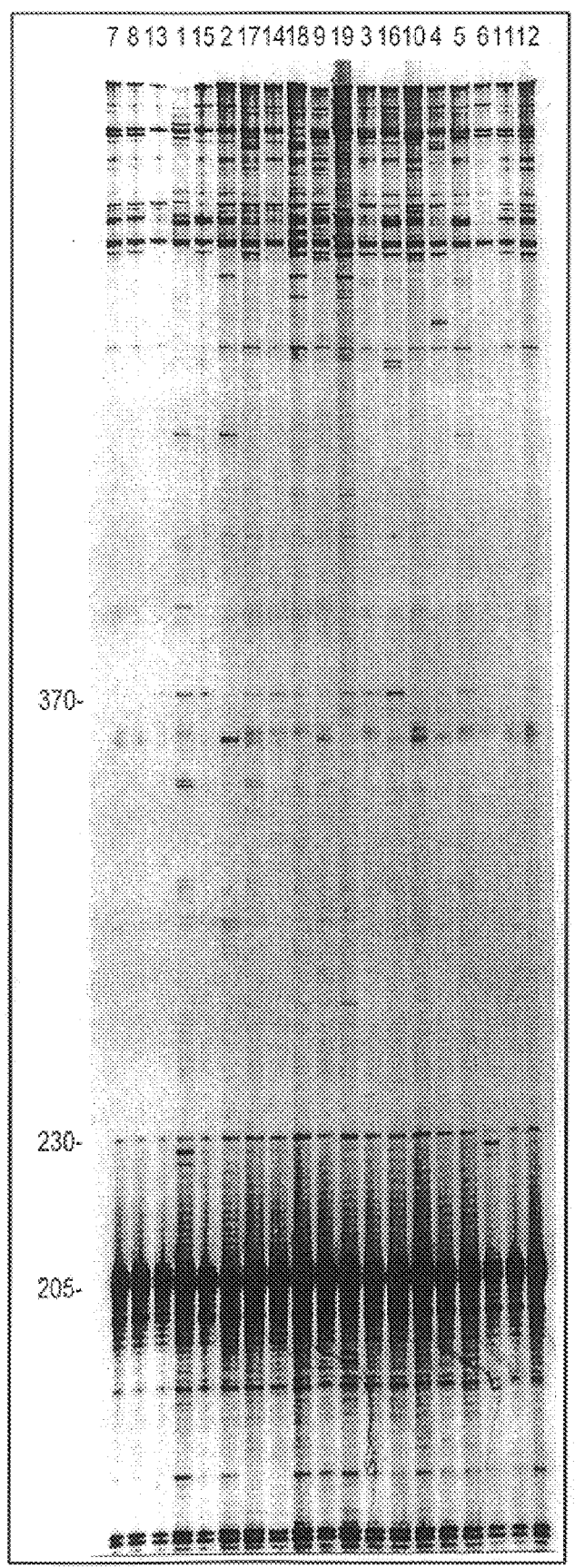

FIG. 9: FIG. 9 is a DNA analysis of grape varieties; for ISTR fingerprint analysis DNA from 19 different grape genotypes was subjected to a PCR reaction with the primer pair ISTR5/ISTR-2(SEQ ID NOS: 5 and 10). In the individual lanes the PCR products of the following plants were applied:

1: Sangiovese piccolo precoce, 2: Sangiovese dell'Elba, 3: Sangiovese polveroso Bonechi, 4: Colorino americano, 5: Prugnolino medio, 6: Colorino del Valdarno, 7: Morellino, 8: Brunellone, 9: Sangiovese forte, 10: Sangiovese R10, 11: Saragiolo, 12: Colorino di Pisa, 13: Prugnolino doice, 14: Morellino di Scansano, 15: Colorino di Lucca, 16: Giacche, 17: Tinturier, 18: Sangiovese polveroso, 19: Prugnolo gentile.

Figure 10A:
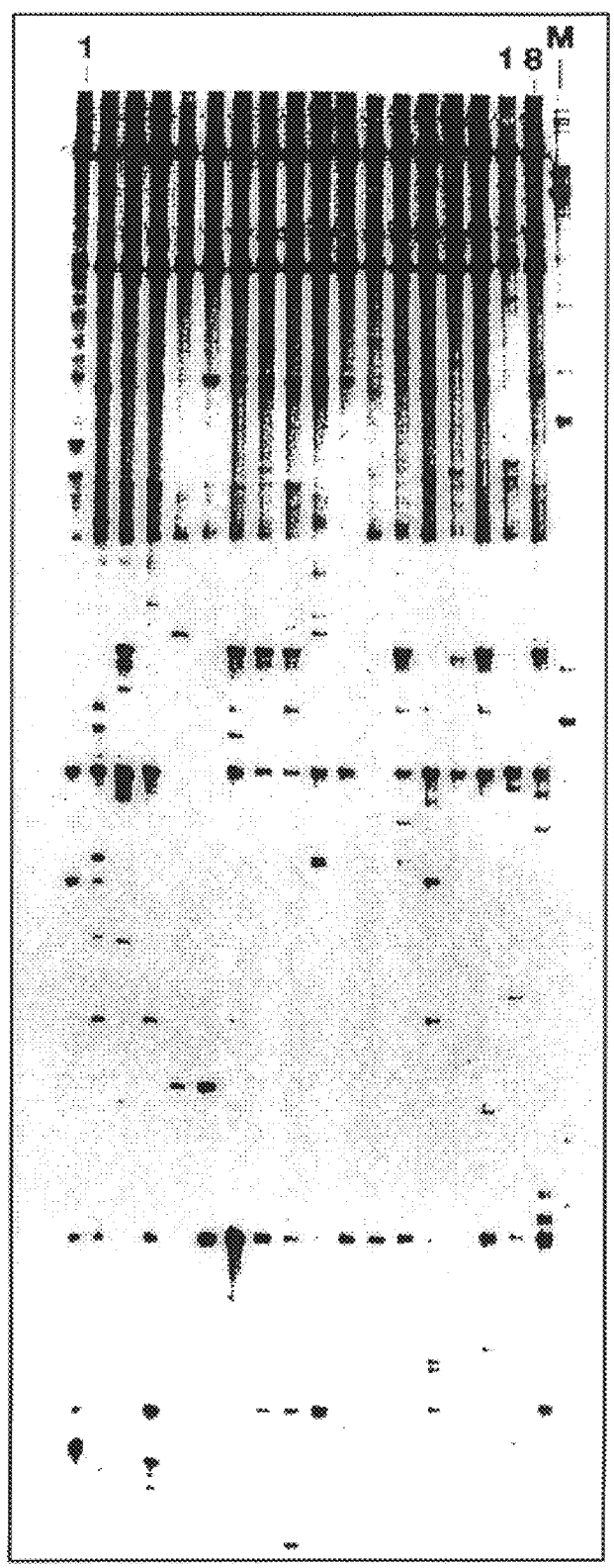

FIGS. 10A, B, C: Analysis of Phytophthora palmivora isolates from the Philippines with the primer combination ISTR5/ISTR-2(SEQ ID NOS: 5 and 10)

1: #P8704 (DRCO89; Davao City, Mindanao); 2: #P8646 (DRC001; Davao Sur, Mindanao); 3: #P8652 (DRC007; Davao City, Mindanao); 4: #P8650 (DRC005; Davao City, Mindanao); 5: #P8698 (DRC082; Zamboanga, Mindanao); 6: #P8684 (DRC065; De Oro City, Mindanao); 7: #P8676 (DRC053; Davao City, Mindanao); 8: #P8653 (DRC008; Davao Norte, Mindanao); 9: #P8647 (DRC002; Davao Norte, Mindanao); 10: #P8649 (DRC004; Davao Norte, Mindanao); 11: #P8662; 12: #P8663 (DRC030; Davao Norte, Mindanao); 13: #P8667 (DRC036; South Cotabato, Mindanao); 14: #P8651 (DRC006; Davao Sur, Mindanao); 15: #P8674 (DRC047; Batangas, Luzon); 16: #P8660 (DRC025; Laguna, Luzon); 17: #P8705 (DRC090; Davao Norte, Mindanao); 18: #P8665 (DRC033; South Cotabato, Mindanao).

M: control reaction with DNA of MRD (Malayan Red Dwarf) coconut palm.

The examples explain the invention.

EXAMPLE 1
Detection of Length Polymorphism in the Coconut

For this experiment as represented in FIG. 3, primer pairs ISTR5/ISTR-2 (SEQ ID NOS: 5 and 10) and ISTR5/ISTR-1 (SEQ ID NOS: 5 and 9) (see Table 1) were used. The DNAs to be analyzed were obtained of single palm trees of populations from East African Tall (EAT) and Malayan Yellow Dwarf (MYD) as well as from a single palm tree Rennel Island Tall (RLT) and Pemba Red Dwarf (PRD). The oligodeoxynucleotides employed (primers) were $^{32}$p radioactively labeled at their ends via polynucleotide kinase by known means and subjected to a PCR reaction. This was conventionally performed in a volume of 20 μl and contained 1 pmol of each of the primers and 25 ng of the genomic DNA to be amplified in 1×PCR reaction buffer (e.g. of the company GIBCO/BRL), 2.5 mM $MgCl_2$, 0.25 mM dNTP (deoxynucleoside triphosphate), and 1 unit Taq DNA polymerase. First the mixture is subjected for three minutes to 95° C. for denaturation followed by 40 cycles of 95° C. (30 seconds, denaturing), 45° C. (30 seconds, annealing) and 72° C. (2 minutes, synthesis). The reaction ends with a step at 72° C. for ten minutes (synthesis), 10 μl of a dye mixture (in formamide) are added and after heating 3 μl thereof are separated on a 4% polyacrylamide sequencing gel. After separation of the glass plates, the gel is dried in a known manner on one of the sequencing plates and the separated radioactively labeled PCR products are made visible by exposure to an X-ray film. This experimental protocol applies also to all other ISTR primers and to the following examples.

As can be inferred from FIG. 3, some of the DNA products are common to all palms but also differences in the individual palm trees of both populations are observed. This is not surprising for the "Tall" type EAT (FIG. 3A), since for this coconut type cross fertilization in the field has been observed. However, surprisingly, the ISTR analysis discovers also differences in the "dwarf" palm type such as MYD which was commonly supposed to be autogamous within the populations as well as differences between the populations from Tanzania and the Philippines (FIG. 3B). Such differences in dwarf populations could not be detected with previously used RFLP markers. Furthermore, it appears that the use of the primer pair ISTR5/ISTR-1 (SEQ ID NOS: 5 and 9) not only - as expected from the position of the ISTR-1 (SEQ ID NO; 9) primer (FIG. 2B)—generates PCR products which are approximately 100 base pairs shorter in length but also causes new polymorphisms. The reason for this can only be speculated on but the finding opens the possibility of using all conceivable copia-like sequences and primer combinations for the ISTR analysis based on the ascertained copia-like sequences in the coconut Thus, this simple experiment impressively demonstrates how a single PCR amplification using the identical primer pair allows a reproducible fingerprint analysis of individual palm trees and statements to the genetic homogeneity of populations.

EXAMPLE 2
Test for a General Application in Plants

In order to find out whether it is generally possible to use the coconut-specific ISTR primers for the detection of DNA polymorphisms in copia-like sequences in plants, for the experiment of Example 2, the genomic DNAs of different plants were subjected to PCR reaction with the ISTR primer pair ISTR5/ISTR-2(SEQ ID NOS: 5 and 10). From FIG. 4 it can be seen that from tobacco to yeast DNA all DNAs give individual PCR products by use of the coconut-specific primers. Similar experiments were also performed with other ISTR primer combinations. This shows that families of adjacent copia-like repetitive elements similar to those described for coconut exist in lower and higher plants and are accessible for fingerprint analysis. As a consequence, the ISTR analysis is not only applicable for a single plant species as described in Example 1 but also for the characterization of genetic diversity and the assessment of plant genetic resources either in gene libraries or by in-situ conservation.

EXAMPLE 3
Test for the Application within a Plant Family Exemplified for Palms (Arecaceae)

The possible application of the ISTR analysis for taxonomic studies was performed with the ISTR primer pair ISTR5/ISTR-2 (SEQ ID NOS: 5 and 10) in plant species of the family Arecaceae (Palmae). In this experiment, DNAs of 17 palm species (see legend of FIG. 5) were amplified in a PCR reaction with the mentioned primers and PCR products were analyzed in a known manner. As can be seen in FIG. 5, for each palm a different fingerprint is obtained, which permits the processing of the data via computer-aided evaluation of a corresponding matrix for the assessment of biological diversity by means of generation of dendrograms according to conventional methods. Important for the practical usability is, for example, which genetic relatedness exists, e.g. between the important oil plants of the oil and the coconut palm. Genetic markers, for example, for the feature of the thickness of the nutshell, which is important for the yield of oil, could be used in both species for breeding purposes if they are genetically highly related.

EXAMPLE 4
Test for Application in Highly Cultivated Varieties Illustrated for Barley Characterization of cultivated varieties via fingerprint analysis by means of the ISTR technology was tested by the example of barley varieties. FIG. 6 shows a PAGE analysis of PCR products which were obtained for a total of 35 varieties and/or genotypes. The high genetic relatedness of the highly cultivated barley varieties investigated is apparent from the high number of monomorphic DNA fragments. However, even in this single analysis a total of 44 polymorphic markers could be identified which were mainly located in the upper part of the sequencing gel. These markers were grouped in a matrix and based on the matrix a dendrogram was evaluated by the UPGMA method. The fact that the variety Bonus (lane 33) could not be distinguished from calcaroides-b19 (lane 32) is not surprising since this genotype is a recessive mutant of Bonus. This, however, holds also true for the genotypes Calcaroides-C15 (lane 30) and calcaroides-b2 (lane 31) which were generated via mutagenesis in the same genetic background. However, in this case, neutron radiation (Calcaroides-C15) and X-radiation (calcaroides-b2) were used as mutagenes, which usually lead to deletions and inversions on the chromosomal level, while calcaroides-b19 was obtained from Bonus via sodium azide treatment, which causes point mutations. Firstly, this example thus illustrates that the ISTR analysis is suitable to give indications of rearrangements of the genetic material. Secondly, the use of a single ISTR primer pair is sufficient for a fingerprint of highly cultivated varieties. Thus, it can be concluded that by using further ISTR primer pairs an unambiguous variety-specific fingerprint can be obtained, which serves for biochemical characterization of the variety (protection of plant varieties).

EXAMPLE 5

Test for Application in Animals: Evidence for Segregating and Newly Developing Markers in Families In order to test general applicability of the ISTR analysis for genetic material outside the plant kingdom, animal families were investigated in which the father was known because of controlled breeding (in-vitro fertilization). FIG. 7 illustrates an ISTR analysis with the primer pair ISTR5/ISTR-2 (SEQ ID NOS: 6 and 9) of a cattle family (FIG. 7A) and of two sheep families with identical father but two different mothers M1 (FIG. 7B) and M2 (FIG. 7C). Both analyses reveal that 1) coconut specific ISTR primers can also be used in the animal kingdom for fingerprint analysis and that 2) segregating markers (see arrows in FIG. 7C) as well as individual specific markers (see asterisks in FIG. 7) are accessible via ISTR analysis. An indication that segregating ISTR markers are capable of cosegregating with important phenotypes is evidenced by the DNA band of the prominent triplet designated as SSM (sex specific marker) in FIGS. 7B, C: This band is present in the father but not in the two mothers. In fact, both of the offspring of family 1 (FIG. 7B) are female while family 2 (FIG. 7C) has a male progeny. The facts that the parental markers are not present in all offspring (see arrow in FIG. 7A) and that new markers developed (see asterisks in FIG. 7), can be interpreted as an indication that the ISTR analysis is capable of discovering recombination events in cross-breedings.

EXAMPLE 6

Test for Application in Humans: Evidence for Sex and Individual-specific Polymorphisms This example illustrates the application of the ISTR analysis in the field of humans. For humans, three families I, II and III were analyzed wherein both children of families I and II were homozygous (identical) twins. Since it could not be expected that ISTR primers were capable of discovering DNA polymorphisms in identical twins (highly polymorphic microsatellite primers do not display any differences, Haas, Institut für Rechtsmedizin, Universitat Giessen; personal communication), 6 different ISTR primers were tested. In all 6 analyses DNA polymorphisms are visible, and two of the ISTR analyses of the primer pairs ISTR6/ISTR-1 (SEQ ID NOS: 6 and 9) and ISTR6/ISTR-2 (SEQ ID NOS: 6 and 10) are shown in FIG. 8. The analysis with the primer pair ISTR6/ISTR-1 (SEQ ID NOS: 6 and 9) (FIG. 8A) is remarkable for the multitude of polymorphic DNA bands which are individual-specific and provide an unambiguous characterization of the individual human even in the two pairs of identical twins of families I and II. This also holds true for the ISTR analysis performed with the primer pair ISTR6/ISTR-2 (SEQ ID NOS: 6 and 10) shown in FIG. 8B, although the number of polymorphic bands is lower. Most remarkably, one DNA band is found among the new polymorphisms (SSM in FIG. 8B) which is only present in the three fathers but not in the three mothers or in the five children. Actually, it is possible that, as mentioned in Example 5 for the sheep families, said DNA band concerns a sex-specific marker since all five children are female and thus a strictly sex-specific segregation within a total of 11 individuals is given.

EXAMPLE 7

Detection of ISTR Fingerprints for Grape Varieties

For this test, which is represented in FIG. 9, the primer pair ISTR5/ISTR-2 (SEQ ID NOS: 5 and 10) (see Table 1) was used. As DNAs to be examined the genomic DNAs of 19 Vitis vinifera L. plants as well as 13 suspected "Sangiovese" genotypes and 6 "colored" ecotypes were used, the fruit of which is of importance for the intensive red coloration of the wine. It is evident from FIG. 9 that a large number of polymorphous DNA fragments was obtained. Although the variability is highest in the "colored" ecotype, ISTR analysis evidenced also a high proportion of polymorphisms in the "Sangiovese" genotypes. These differences can possibly be ascribed to the polyclonal origin of many grape cultivars. Therefore, this example, too, proves that ISTR analysis is an efficient and sensitive method for examining the genetic diversity within ecotypes and for the identification of individual clones.

EXAMPLE 8

Use of the ISTR Fingerprints in Microorganisms

The use of the ISTR technique in microorganisms was exemplified for isolates of the fungus Phytophthora palmivora which induces lethal diseases ("bud rot") in coconut palms. A particularly difficult example was chosen for the use of a DNA marker technology for which, due to the limited genetic diversity, originally only few polymorphisms were expected since in all cases P. palmivora isolates were used which were moreover exclusively isolated in the Philippines and were locally limited (the isolates were mainly derived from Mindanao island).

Figure 10B:
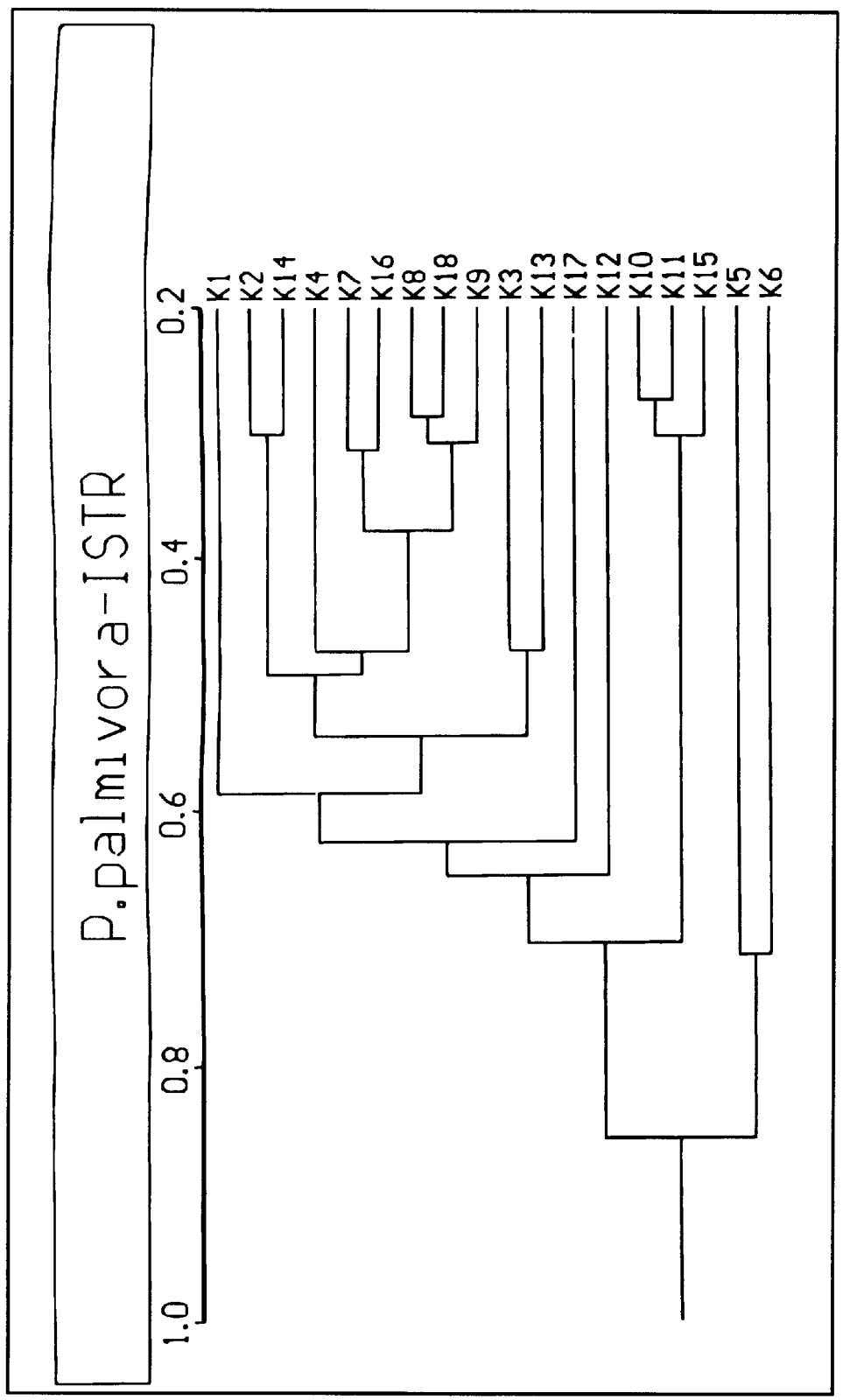
Figure 10C:
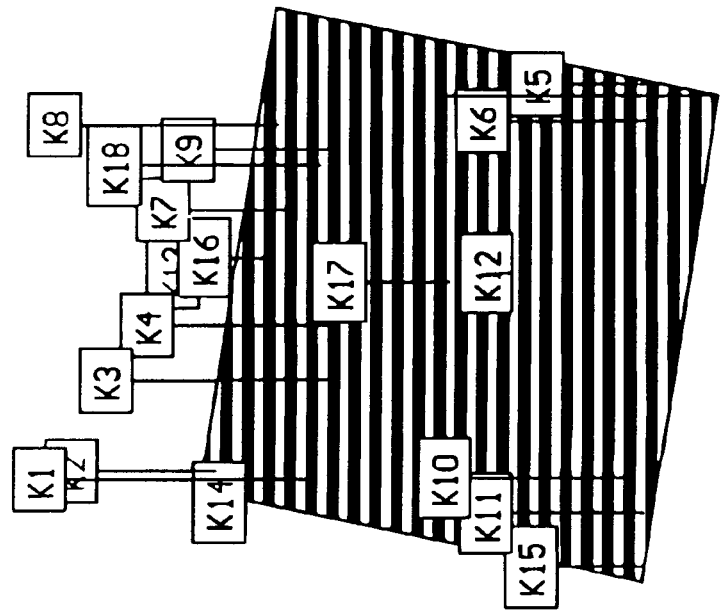

1 µg DNA each was amplified of eighteen P. palmivora isolates from the Philippines in a standard PCR reaction with the primer combination ISTR5/ISTR-2(SEQ ID NOS: 5 and 10), the products were separated by PAGE on a 4% polyacrylamide gel in a conventional manner and the individual bands were visualized by autoradiography. FIG. 10 shows the result of this analysis. Already the gel analysis (FIG. 10A) yields a large variety of polymorphous DNA fragments with a single ISTR primer combination. Thirty of these bands were analyzed according to the known method of the cluster analysis to phenograms according to the UPGMA method (SAHN clustering; FIG. 10B) and by PCA (principal coordinate analysis; FIG. 10C). The data obtained corresponded well to the classification of these isolates using the RAPD-DNA marker analysis.

TABLE 1

Examples of oligodeoxynucleotides (ISTR primer) used for the ISTR analysis
ISTR primer sequence (5'→3')

Forward primer

ISTR1 SEQ ID NO:1 AGG AGG TGA ATA CCT TAG

ISTR2 SEQ ID NO:2 AAA ATG GCA TAG TCT CTC

ISTR3 SEQ ID NO:3 GTC GAC ATG CCA TCT TTC

ISTR4 SEQ ID NO:4 TAT AGT ACC TAT TGG GTG

ISTR5 SEQ ID NO:5 ATA TAT GGA CTT AAG CAA GC

ISTR6 SEQ ID NO:6 GTA TTG TAC GTG GAT GAC ATC

ISTR7 SEQ ID NO:7 CAA CAG TGC TCC CAC TGA

TABLE 1-continued

Examples of oligodeoxynucleotides (ISTR primer) used for the ISTR analysis
ISTR primer sequence (5'→3')

ISTR7 SEQ ID NO:8 TGC TAG GAC TTT CAC AGA

Backward primer

ISTR-1 SEQ ID NO:9 TTT TCT ACT TCA TGT CTG A

ISTR-2 SEQ ID NO:10 AAT AAA TCG ATC ATC GAC

ISTR-3 SEQ ID NO:11 ATT CCC ATC TGC ACC AAT

ISTR-4 SEQ ID NO:12 ATG TCA TCC ACG TAC AAT

ISTR-5 SEQ ID NO:13 CTT CTG TGA AAG TCC TAG

---

What is claimed is:

1. A method for DNA fingerprint analysis consisting essentially of annealing a single primer consisting of 15–25 contiguous nucleotides of the complement of a 1.4 kilobase-pair copia-like element of the DNA of *Cocos nucifera L.* to a sample of genomic DNA, obtaining a plurality of polymerase chain reaction products products by performing a polymerase chain reaction using said single primer and obtaining a DNA fingerprint by separating the polymerase chain reaction products.

2. The method of claim 1, wherein said genomic DNA is obtained from a human, a non-human animal, a plant or a microorganism.

3. The method of claim 1, wherein said genomic DNA is obtained from a human, a non-human animal or a plant.

4. The method of claim 1, wherein said genomic DNA is obtained from an organism that is a mammal, a monocotyledenous plant or a dicotyledenous plant.

5. The method of claim 1, wherein said genomic DNA is obtained from an organism of the family Hominidae, Bovidae, Arecaceae or Poaceae.

6. The method of claim 1, wherein said genomic DNA is obtained from an organism of the genus Homo, Bovis, Ovis, Hordum, Zea, Solanum, Nicotiana, Petunia, Brassica, Beta, Vitus or Neisseria.

7. A The method of claim 1, wherein said genomic DNA is obtained from a fungus, a lactic acid bacterium, a sarcina bacterium, a coryneform bacterium or a gram-negative bacterium.

8. The method of claim 1, wherein said genomic DNA is obtained from a fungus that is of the family Phytophthora or Ascomycetes.

9. The method of claim 1, wherein said primer has a nucleotide sequence of any one of SEQ. ID. NOS: 1 to 13.

10. The method of claim 1, wherein said separating step comprises separating said polymerase chain reaction products on a sequencing gel.

11. The method of claim 1, further comprising Southern blotting said polymerase chain reaction products.

12. The method of claim 11, wherein said Southern blotting is performed using as a probe a labeled oligonucleotide having a nucleic acid sequence of any one of SEQ. ID. NOS.: 1 to 13.

13. The method of claim 12, wherein said label is digoxigenin, biotin, a fluorescent dye or a radioactive label.

14. The method of claim 1, wherein said copia-like element comprises a Sal I restriction site and a Sca I restriction site.

15. The method of claim 1, wherein said primer is from 15 to 25 nucleotides in length.

16. A method for DNA fingerprint analysis comprising annealing at least one primer consisting of 15–25 contiguous nucleotides of the complement of a 1.4 kilobasepair copia-like element of the DNA of *Cocos nucifera L.* to a sample of genomic DNA, wherein said sample of genomic DNA is obtained from an organism other than a plant of the genus Cocos, obtaining a plurality of polymerase chain reaction products by performing a polymerase chain reaction and obtaining a DNA fingerprint by separating the polymerase chain reaction products.

17. The method according to claim 16, wherein a pair of primers is utilized in said polymerase chain reaction.

18. The method of claim 16, wherein said at least one primer is from 15 to 25 nucleotides in length.

19. The method of claim 17, wherein said pair of primers is SEQ ID NOS: 5 and 9.

20. The method of claim 17, wherein said pair of primers is SEQ ID NOS: 5 and 10.

21. The method of claim 17, wherein said pair of primers is SEQ ID NOS: 6 and 9.

22. The method of claim 17, wherein said pair of primers is SEQ ID NOS: 6 and 10.

23. The method of claim 17, wherein said pair of primers consists of a first primer selected from the group consisting of SEQ ID NOS: 1–7 and a second primer selected from the group consisting of SEQ ID NOS: 9–13.

24. The method of claim 16, wherein said genomic DNA sample is obtained from a human, a non-human animal or a microorganism.

25. The method of claim 16, wherein said organism is a monocotyledenous plant.

26. The method of claim 16, wherein said genomic DNA is obtained from an organism of the family Hominidae, Bovidae, Arecaceae or Poaceae.

27. The method of claim 16, wherein said genomic DNA is obtained from an organism of the genus Homo, Bovis, Ovis, Hordum, Zea, Solanum, Nicotiana, Petunia, Brassica, Beta, Vitus or Neisseria.

28. The method of claim 16, wherein said genomic DNA is obtained from a fungus, a lactic acid bacterium, a sarcina bacterium, a coryneform bacterium or a gram-negative bacterium.

29. The method of claim 16, wherein said genomic DNA is obtained from a fungus that is of the family Phytophthora or Ascomycetes.

30. The method of claim 16, wherein each of said at least one primer has a nucleotide sequence of any one of SEQ. ID. NOS.: 1 to 13.

31. The method of claim 16, wherein said separating step comprises separating said polymerase chain reaction products on a sequencing gel.

32. The method of claim 16, further comprising Southern blotting said polymerase chain reaction products.

33. The method of claim 32, wherein said Southern blotting is performed using as a probe a labeled oligonucleotide having a nucleic acid sequence of any one of SEQ. ID. NOS.: 1 to 13.

34. The method of claim 33, wherein said label is digoxigenin, biotin, a fluorescent dye or a radioactive label.

35. The method of claim 16, wherein said copia-like element comprises a Sal I restriction site and a Sca I restriction site.

36. A primer pair selected from the group consisting of SEQ ID NOS:5 and 10, SEQ ID NOS: 6 and 9, and SEQ ID NOS:6 and 10.

\* \* \* \* \*